United States Patent [19] [11] Patent Number: 4,678,459
Onik et al. [45] Date of Patent: Jul. 7, 1987

[54] IRRIGATING, CUTTING AND ASPIRATING SYSTEM FOR PERCUTANEOUS SURGERY

[75] Inventors: Gary Onik, San Francisco; Leonard Ginsburg, Oakland, both of Calif.

[73] Assignees: E-Z-EM, Inc., Westbury, N.Y.; Surgical Dynamics, Incorporated, San Leandro, Calif.

[21] Appl. No.: 633,514

[22] Filed: Jul. 23, 1984

[51] Int. Cl.⁴ ............................................. A61B 17/32
[52] U.S. Cl. ........................................ 604/22; 128/305
[58] Field of Search .................... 128/305, 305.1, 751, 128/752, 755; 604/22

[56] References Cited
U.S. PATENT DOCUMENTS

| | | | |
|---|---|---|---|
| 3,815,604 | 6/1974 | O'Malley et al. | 128/305 X |
| 3,844,272 | 10/1974 | Banko | 128/305 X |
| 3,884,238 | 5/1975 | O'Malley et al. | 128/305 |
| 4,210,146 | 7/1980 | Banko | 128/305 |
| 4,513,745 | 4/1985 | Amoils | 128/305 |
| 4,517,977 | 5/1985 | Frost | 604/22 X |

FOREIGN PATENT DOCUMENTS 1235321 6/1971 United Kingdom ............. 128/305.1
2018601 10/1979 United Kingdom ................ 128/305

Primary Examiner—Michael H. Thaler
Attorney, Agent, or Firm—McAulay, Fields, Fisher, Goldstein & Nissen

[57] ABSTRACT

A percutaneous discectomy system 10 includes a discectomy device 12 having a needle 16 with a port 48 and a flared cutting edge 44 which is actuated past the port 48 to sever tissue provided adjacent thereto. An irrigation device is 18 are provided for irrigating the area adjacent the tip 46 of the needle 16 to assist a vacuum device 22 in aspirating the severed tissue away from the disc. The discectomy system 10 assists in the removal of herniated disc tissue in order to relieve pressure on the nerves located adjacent thereto. In addition, the needle 16 is flexible so that it can be temporarily or permanently bent around other body tissues such as the pelvis in order to access discs which are surgically hard to reach otherwise.

13 Claims, 9 Drawing Figures

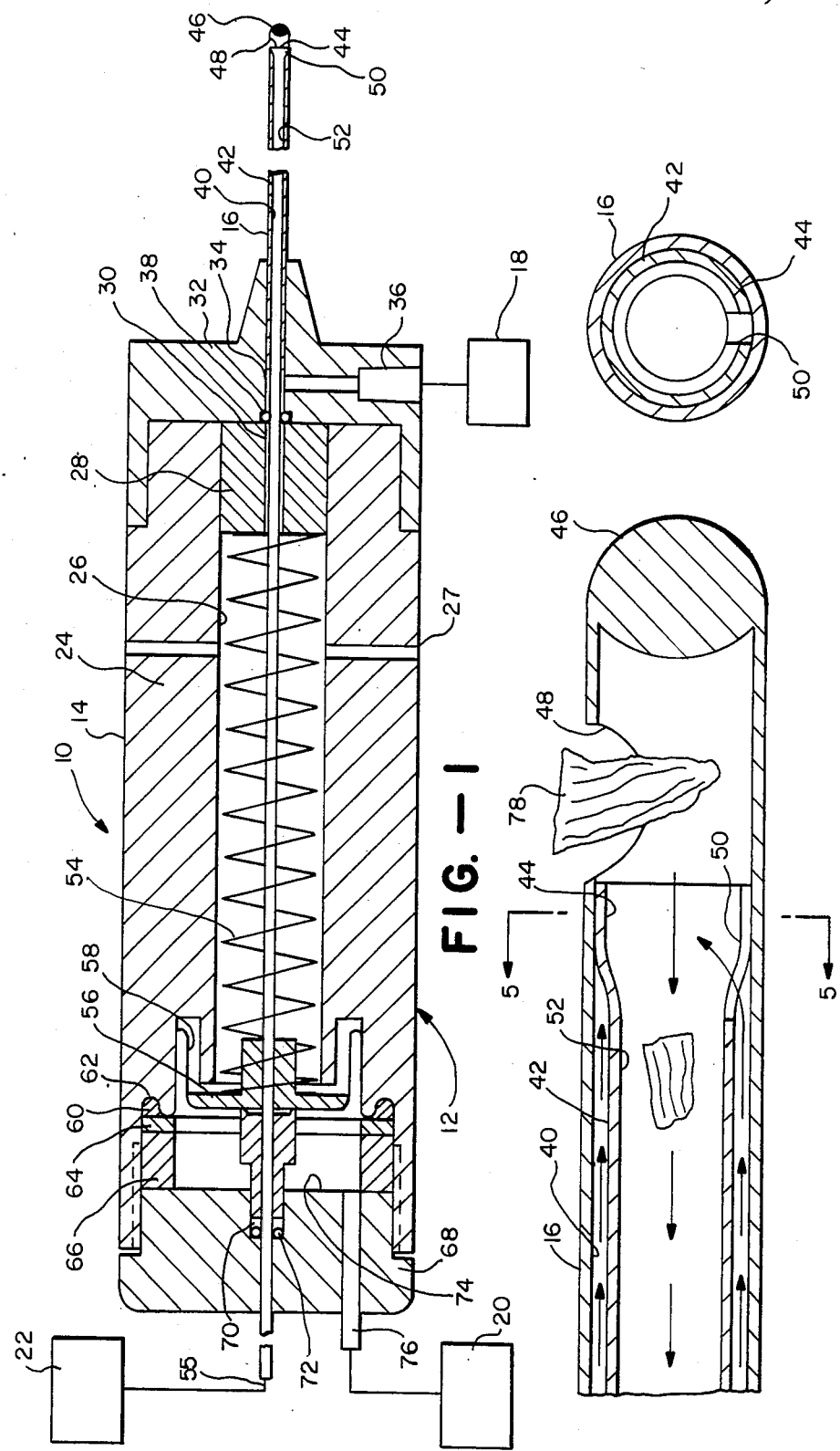

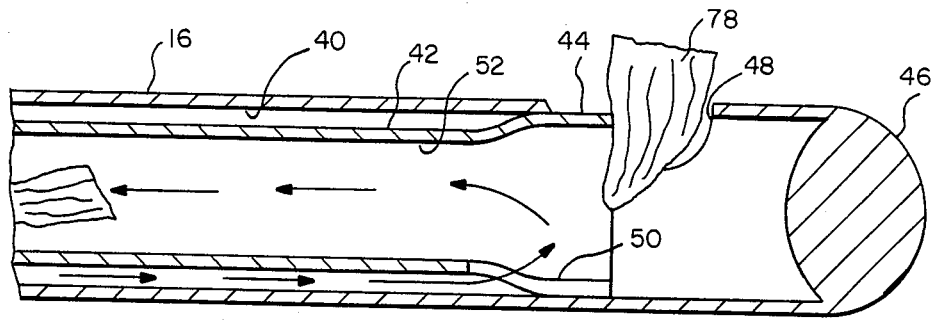
FIG.—3
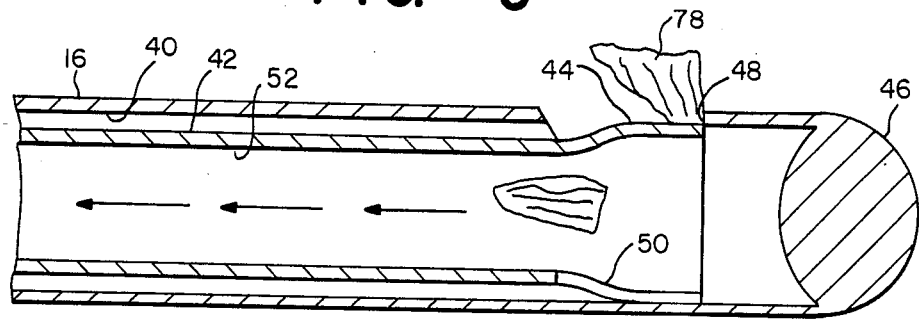
FIG.—4
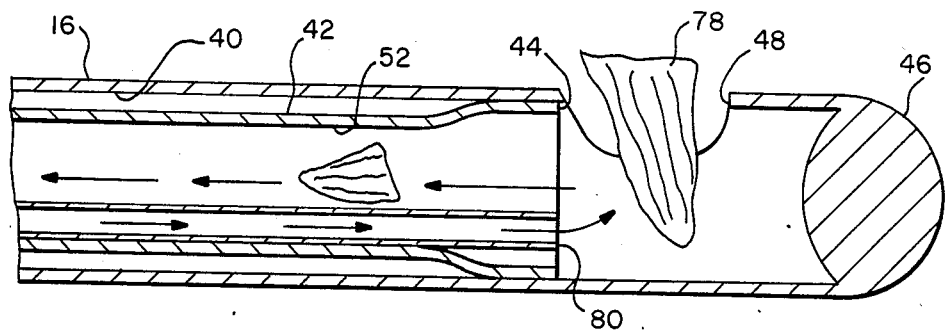
FIG.—6
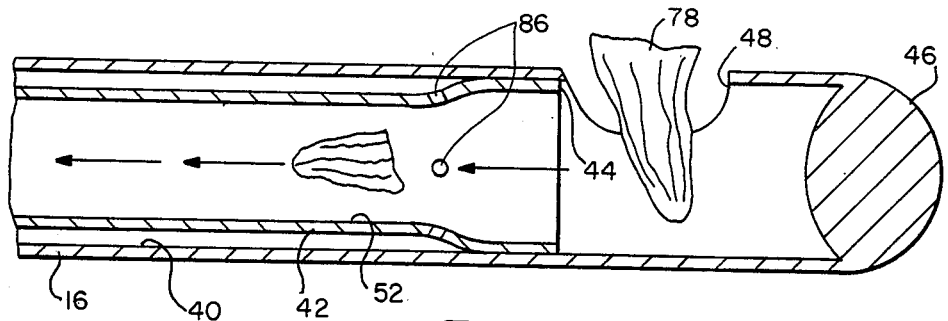
FIG.—7

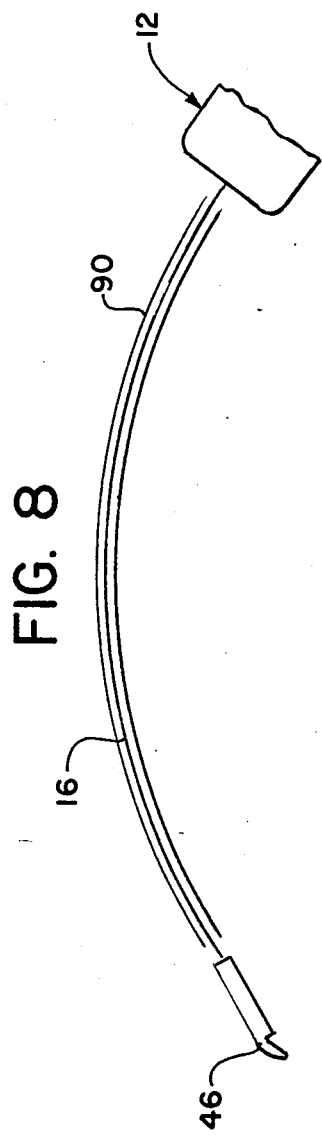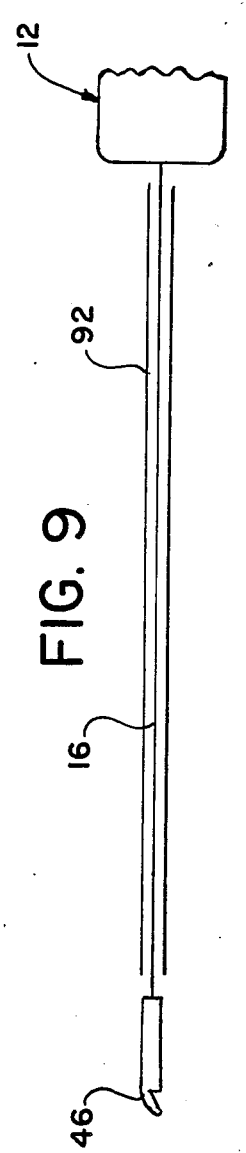

IRRIGATING, CUTTING AND ASPIRATING SYSTEM FOR PERCUTANEOUS SURGERY

TECHNICAL FIELD

The present invention relates to a surgical cutting device and, in particular, to a percutaneous discectomy device for removing nucleus pulposus from a herniated spinal disc.

BACKGROUND ART

An estimated eight million Americans suffer chronic low back pain due to disc problems requring a total disability health care expenditure of over twenty billion dollars. The interverebrate disc can be looked upon as an osmotic system. Bacuse of a breakdown of macromolecules as a person ages, the number of particles in the internal softer tissue of the disc, known as nucleus pulposus, increases and causes a rise in osmotic pressure, which in turn causes a fluid influx into the disc and raises the intradisc pressure. Concomitantly, fissures begin to form in the fibrous annulus, which defines the outer periphery of the disc, because of the biomechanical forces placed upon it. Accordingly, the intervertebral disc may extend through the annulus thereof and compress nerve roots, causing great pain. The remedy has been in the past to reduce the mechanical forces that were causing the increase in disc pressure by placing the patient in bed. When such conservative therapy failed, the surgical approach was followed.

A current surgical approach aims at a total disc removal through a partial hemilaminectomy and thus entails the risks that are associated with major surgery and general anesthesia. In addition, costs of this surgery and the in-hospital convalescence required are large.

Chemonucleolysis has been tried to avoid these problems. The intradiscal pressure is decreased by the percutaneous introduction of chymopapain into the intervertebral disc to dissolve it. Such an approach is effective in the majority of patients but does has some side effects, as some patients are hypersensitive to the drug.

SUMMARY OF THE INVENTION

The present invention is directed to overcoming all of the problems associated with prior surgical and drug treatments by providing a percutaneous discectomy system which can selectively remove herniated disc tissue in a surgical procedure which does not have the traumatic effect on the patient associated with prior surgical procedures. The guillotine type cutting action of the system can effectively cut the herniated disc tissue into small portions while the irrigation and vacuum means of the system can efficiently aspirate the severed herniated disc material and remove same from the disc, decompressing the disc so as to relieve the pressure. Such a procedure can allow the patient to be up and about almost immediately after the procedure has been performed.

The present invention includes a percutaneous discectomy system for removing intervertebral disc tissue which comprises a probe including an elongate tubular member with an elongate central bore and port communicating through the tubular member with the central bore. The device further includes means for cutting the nucleus pulposus of the intervertebral disc, said means including another elongate tubular member having another central bore and a flared cutting edge. The another elongate tubular member is inserted into the central bore of the elongate tubular member and substantially spaced from said central bore of the needle, with the flared cutting edge contacting the central bore of the needle and positioned adjacent the port. The another elongate tubular memeber includes a slot provided through the flared cutting edge so that the space between the central bore and said another elongate tubular member communicates with the another central bore.

In another aspect of the invention, means are provided for communicating internal irrigating fluid in the space defined between the central bore of the needle and the another elongate tubular member of the cutting means. This fluid is used to irrigate the area around the port and the flared cutting edge and to act as a vehicle for the removal of the severed tissue. The general prior art includes probe type guillotine cutters which have a source of irrigating fluid provided externally to the needle adjacent a port. Such probes with external irrigation have not proven successful for aspirating disc tissue.

Additionally, to facilitate the removal of the severed tissue, a source of vacuum is adapted to communicate with the another central bore of the cutting means so as to aspirate the severed tissue.

Still further means are provided for driving the flared cutting edge past the port of the needle in a pulsed manner.

Accordingly, the present invention provides for a percutaneous discectomy device which allows the selected removal of herniated disc tissue without the major surgical implications of standard back surgery and without the side effects of chemical surgery. This system allows the surgery to occur rapidly without the trauma to the patient which is characteristic of other surgical techniques. The invention provides a guillotine cutting arrangement, irrigation system and vacuum or aspiration system which addresses the problem of cutting and removing disc tissue, which is often dry and tough.

In another aspect of the invention, both the needle and the cutting means are flexible so that if the disc tissue is difficult to reach, the needle and cutting means can be bent to curve around bone and tissue structures and address the proper disc without the requirement to drill through, for example, the pelvic bone. This is particularly important for the disc located between the fifth lumbar vertebra and the first sacroiliac vertebra. It is to be understood that the teachings of the present invention can be applied to other than percutaneous discectomy and fall within the scope of the claimed invention.

BRIEF DESCRIPTION OF THE FIGURES

FIG. 1 is a partial schematic, partial section view of an embodiment of the invention.

FIG. 2 depicts a cross-sectional view of the tip of the needle of the embodiment of the invention of FIG. 1.

FIG. 3 depicts a cross-sectional view similar to FIG. 2 with the cutting edge of the embodiment positioned midway through a cut.

FIG. 4 is a figure similar to FIG. 2 with the cutting edge all of the way through a cut.

FIG. 5 is a cross-sectional view taken throuh the line 5—5 in FIG. 2.

FIG. 6 is an alternative embodiment of the invention.

FIG. 7 is yet another alternative embodiment of the invention.

FIG. 8 is a schematic view of the needle positioned within a curved cannula sleeve, with the operative end of the needle exposed to remove disc tissue.

FIG. 9 is a view similar to FIG. 8 showing the cannula sleeve straight instead of being curved.

DETAILED DESCRIPTION OF THE PREFERRED EMBODIMENT

With respect to the figures and in particular to FIG. 1, an embodiment of the percutaneous discectomy system of the invention is depicted and identified by the numeral 10. This descectomy system includes a hand-held percutaneous discectomy probe 12 which has a probe body 14 and a probe needle 16. The system further includes in a preferred embodiment a device 18 for providing and controlling internal irrigation fluid under pressure, a device 20 for providing a pulsed source of positive pressure to drive the system and a device 22 for providing a source of vacuum and collection means for aspirating cut disc tissue. Devices 18, 20, 22 can be included in a single control device console if desired.

The body 14 is comprised of a cylindrical housing 24 which has a central bore 26 and a back pressure relief vent 27. Disposed at one end of the central bore 26 is a plug 28 which has a bore 30 provided therethrough. At the front end of the body 14 is a cap 32 which is secured to the body 14 with glue or other appropriate means. The cap 32 includes a bore 34. Needle 16 is partially inserted into bore 34 and, in a preferred embodiment, glued in place. An irrigation passage 36 communicates with bore 34 at a point adjacent the end of needle 16. This irrigation passage 36 also communicates with the irrigation fluid device 18. The needle 16 defines a central bore 40. Located inside of the central bore 40 of needle 16 and the bore 30 of plug 28 and also the central bore 26 of cylindrical housing 24 is an elongate tubular cutting member 42 which has a flared cutting edge 44 located adjacent the blunt end 46 of the needle 16. An O-ring 38, located in a groove defined by cap 32 and located adjacent the plug 28, provides a seal about tubular member 42.

As will be described more fully hereinbelow, the flared cutting edge 44 is positioned to pass across port 48 located adjacent blunt end 46 and provided through the needle 16. The flared cutting edge 44 has a slot 50 therethrough which provides communication between a central bore 52 of the elongate tubular cutting member 42 and the space located between the central bore 40 of the needle 16 and the elongate tubular cutting member 42. The flared cutting edge 44 is compressed when it is inserted in the central bore 40 of needle 16 in order to increase the effectiveness of the guillotine cutting action of device 12. The fact that the rest of the tubular cutting member 42 is spaced from the central bore 40 of needle 16 not only allows the flow of irrigating fluid, as described below, but also reduces friction between the needle 16 and member 42.

Provided in the central bore 26 and located about the cutting member 42 is a spring 54. Secured to elongate tubular cutting member 42, at the opposite end from cap 32, is a piston 56. Secured to piston 56 is a flexible diaphragm 58. Diaghragm 58 includes a peripheral lip 60 which is seated in annular groove 62 defined by cylindrical housing 24.

A ring member 64 is disposed against the peripheral lip 60 and held in place by a threaded ring 66. This allows the threaded ring 66 to be tightened against the ring 64 which holds the peripheral lip 60 of the diaphragm 58 in place without causing the diaphragm to be pinched or twisted from its position. It is to be understood that upon assemble, the diaphragm is positioned so that the slot 50 in the flared cutting edge 44 is located opposite the port 48 at the blunt end 46 of the needle 16.

Another cap 68 is provided adjacent the piston 56 and includes a threaded portion which can be threaded to the body 14 adjacent the threaded ring 66. A chamber 74 is defined between the cap 68 and the diaphragm 58. The cap 68 includes a central bore 70 which guides a portion of the piston 56 and cutting member 42 and which provides a position to seat an O-ring 72, which provides a seal between the elongate tubular cutting member 42 and the another cap 68. The spring 54 biases the piston 56 and the cutting member 42 against the cap 68 so as to keep the flared cutting edge 44 in a first position located adjacent the port 48 as shown in FIG. 2.

The vacuum source device 22 is provided in communication with the central bore 52 of the elongate tubular cutting member 42 aspiration line 55, and the pulsed pressure device 20 is provided in communication with the chamber 74 through a passage 76 provided in the another cap 68.

The various positions which the cutting edge 44 can occupy relative to the port 48 are shown in FIGS. 2, 3, 4. In FIG. 2, a first position is shown with the port 48 fully open. In FIG. 3, the cutting edge 44 is urged toward the blunt end 46 by pulsed pressure provided to the chamber 74 from the pressure device 20 to capture and sever a piece of disc tissue 78. In FIG. 4, the cutting edge 44 has passed completely by the port 48 and has severed the tissue 78 whereby, with the aid of the irrigating fluid shown by the arrows and the vacuum provided by device 22, the severed tissue is aspirated into a collection bottle of the device 22. A cross-sectional view of the needle including the slot of the cutting edge 44 is depicted in FIG. 5.

In a preferred embodiment, the housing 14 can be comprised of plastic or other suitable materials, and the needle 16 and the tubular cutting member 42 can be comprised of flexible stainless steel tubing with the elongate tubular cutting member 44 chrome-plated to prevent galling. The needle and cutting member 42 can be permanently bent to a fixed orientation if desired or can be temporarily bent if it is provided through a bent sleeve as will be described hereinbelow.

In a preferred embodiment, the diameter of the needle 16 is 0.084 inches, or approximately 2 millimeters, while the internal diameter of the central passage 40 of the needle 16 is approximately 0.073 inches with the outer diameter of the tubular cutting member 42 being approximately 0.059 inches. This spacing provides for sufficient irrigating fluid to be provided to slot 50 in order to provide irrigation adjacent the port 48.

It is to be understood that other types of cutting arrangement such as rotating cutters can be used and be within the scope and spirit of the invention.

Alternate embodiments of the invention are depicted in FIGS. 6 and 7. In FIG. 6, an additional elongate tube 80 is provided inside the central bore 52 of the tubular cutting member 42. Irrigation fluid can be provided therethrough into the area adjacent the port 48. In the other embodiment depicted in FIG. 7, apertures 86 are provided through the flared portion of member 42 adjacent cutting edge 44. Apertures 86 provide internal irrigation fluid communication and allow for a strong cutting edge 44.

It is to be understood that with internal irrigation as provided by the present invention, irrigation fluid tends not to pass through port 48 and thus does not interfere with the sucking of tissue into port 48.

It is also to be understood that in addition to pulsing the source of positive pressure to drive diaphragm 58 and thus to drive the cutting edge 44, the irrigation fluid from device 18 as well as the vacuum from device 22 is also pulsed as follows. The irrigation fluid is periodically pulsed off or to a reduced flow with the port 48 open so as not to reduce the vacuuum and the efficiency thereof in pulling tissue into the port. As cutting is completed and the cutting edge 44 closes port 48, the irrigation fluid is pulsed on to assist in removing the severed tissue through aspiration line 55. The vacuum is pulsed to prevent clogging of tissuue in aspiration line 55 by providing an impulse to such tissue.

It is further to be understood that device 18 can also control the irrigation fluid flow rate independently of the above periodic pulsed flow rate. This second control can be adjusted by the operator by observing the flow of irrigation fluid and tissue in the aspiration line 55 which in a preferred embodiment is substantially clear. If the operator observes a fast irrigation fluid flow with little tissue, the operator can decrease generally the flow rate independently of the first periodic pulsed flow rate so that the vacuum can be more efficient in aspirating tissue. If the operator observes a slow irrigation flud flow rate with much tissue, the operator can generally increase the fluid flow rate as a preventative measure so that tissue clogging does not occur.

INDUSTRIAL APPLICABILITY

The operation of the percutaneous discectomy system 10 is as follows. Using CT scan techniques and the like, the needle 16 can be inserted straight-in between the appropriate vertebra and into the herniated disc. Prior to the insertion of the needle 16, a small hole can be prepared through the fibrous annular ring which defines the outer periphery of the disc. The needle is then inserted through this opening.

As the needle 16 is inserted through the hole drilled in the periphery of the disc, the irrigation device, the suction device, and positive pressure device are turned on to operate the guillotine cutting action of the flared cutting edge 44 relative to the port 48 and to aspirate tissue. As the needle is inserted further into and through the disc, additional tissue is severed and aspirated. Also as the needle is rotated in place, the port 48 is exposed to different portions of the disc and additional tissue is severed and aspirated. Once the required amount of tissue is removed, the needle can be moved from the disc.

It is to be understood that if the disc is located in a hard-to-reach area such as between the fifth lumbar and the first sacroiliac vertebrae, then instead of cutting through part of the pelvis or other tissues or bone structures, an introduction and delivery system which includes a curved sleeve or cannula as shown in FIG. 8 can be inserted using known techniques, such as with the aid of the CT scan so as to avoid the bone obstacles. Such an introduction and delivery system using a straight sleeve 92 as shown in FIG. 9 can also be used, if desired, in the above described straight-in procedure. Once the cannula 90, 92 is positioned, the flexible needle can be inserted through the cannula into the disc so as to remove disc tissue along a linear path. It is to be understood that the port 48 can also be rotated throughout 360° in order to extract additional tissue. Further it is to be understood that if desired, the needle 16 can be permanently bent, and without the use of a sleeve or cannula can be inserted into this position. However, there is then no opportunity to rotate the port 48 located in the needle 16 in order to sever and aspirate tissue on a 360° basis. It is also to be understood that such an introduction and delivery system can be used generally with this invention and can also include devices for precisely maintaining the position of the probe relative to the body.

From the above it can be seen that the present invention provides for a system for removing tissue from a herniated disc without causing undue trauma to the patient. Additionally the system is flexible so that it can be positioned in otherwise surgically hard to reach areas, plus it provides for irrigation of the severed material to facilitate the aspiration thereof to the collection vessel. The pulsed vacuum creates impulses in the line which act as shock waves to further facilitate the aspiration of the tissue and prevent it from clogging in the needle 16.

Other advantages of the invention can be obtained from a review of the figures and the appended claims. It is to be understood that although the present invention was described relative to a percutaneous discectomy procedure, that a similar system can be used to remove tissue from other portions of the body or for other unrelated purposes and fall within the scope of the invention and the appended claims.

I claim:
1. A surgical instrument comprising:
   a housing;
   a needle supported by said housing, said needle having a forward portion extending distally of said housing;
   said needle including a first elongated tubular wall member defining a first bore, and having a port formed entirely within the sidewall of the forward portion of said first tubular wall member;
   said needle including a second elongated tubular wall member defining a second bore sized to permit passage of tissue therethrough when said second tubular wall member is connected to a source of suction, said second tubular wall member having a forward portion extending radially outwardly and terminating in a cutting edge;
   said second tubular wall member being positioned within said first tubular wall member with said cutting edge in contact with the sidewall defining said first bore, the forward portion of said first bore adjacent said port defining a tissue receiving portion communicating with said second bore;
   said first and second tubular wall members being the only tubular wall members in said forward portion of said needle;
   the wall of said second tubular wall member spaced inwardly from the wall of said first tubular wall member to define the opposing walls of an annular passageway adapted to be connected to a source of irrigating fluid, said annular passageway being the sole annular chamber in said forward portion of said needle;
   said second tubular wall member being disposed for movement within said first tubular wall member to cause said cutting edge to move from a first position where tissue is drawn through said port into said tissue receiving portion of said first bore under suction to a second position where said cutting edge traverses said port to sever the tissue drawn therethrough, and to permit the severed tissue to be captured in said tissue receiving portion;

said second tubular wall member having an opening formed in its sidewall adjacent said cutting edge to provide internal communication between said annular passageway and said second bore to permit direct passage within said needle of irrigating fluid between said annular passageway and said second bore;

the forward portion of the sidewall of said first tubular wall member having no opening rearward of said cutting edge of said second tubular wall member when said cutting edge is in its first position;

whereby the severed tissue is evacuated through said second bore with the aid of the irrigating fluid.

2. The surgical instrument of claim 1 wherein said first tubular wall member has a cylindrical surface defining said sidewall and a blunt end wall, said port in said sidewall located adjacent said blunt end.

3. The surgical instrument of claim 1 further comprising means for moving said cutting edge of said second tubular wall member between its first and second positions.

4. The surgical instrument of claim 3 wherein said moving means includes a diaphragm associated with said second tubular wall member, and means for exposing said diaphragm to a source of pulsating positive pressure.

5. The surgical instrument of claim 1 further comprising means for providing the irrigating fluid to said annular passageway.

6. The surgical instrument of claim 5 further comprising means for regulating the flow of the irrigating fluid.

7. The surgical instrument of claim 1 further comprising means for providing the source of suction to said second tubular wall member.

8. The surgical instrument of claim 1 wherein the flow of irrigating fluid is "off" when said cutting edge is in its first position and "on" when said cutting edge is in its second position;

9. The surgical instrument of claim 1 further comprising a cannula adapted to receive said first tubular wall member.

10. The surgical instrument of claim 9 wherein said cannula is curved, said first and second tubular wall members being sufficiently flexible to fit within said curved cannula.

11. The surgical instrument of claim 1 wherein said instrument is a percutaneous discectomy device.

12. A percutaneous discectomy surgical instrument comprising:

a housing;

a needle supported by said housing, said needle having a forward portion extending distally of said housing;

said needle including a second elongated tubular wall member defining a second bore sized to permit passage of tissue therethrough when said second tubular wall member is connected to a source of suction, said second tubular wall member having a forward portion extending radially outwardly and terminating in a cutting edge;

said second tubular wall member being positioned within said first tubular wall member with said cutting edge in contact with the sidewall defining said first bore, the forward portion of said first bore adjacent said port defining a tissue receiving portion communicating with said second bore;

said first and second tubular wall members being the only tubular wall members in said forward portion of said needle;

the wall of said second tubular wall member spaced inwardly from the wall of said first tubular wall member to define the opposing walls of an annular passageway adapted to be connected to a source of irrigating fluid, said annular passageway being the sole annular chamber in said forward portion of said needle;

said second tubular wall member being disposed for movement within said first tubular wall member to cause said cutting edge to move from a first position where tissue is drawn through said port into said tissue receiving portion of said first bore under suction to a second position where said cutting edge tranverses said port to sever the tissue drawn therethrough, and to permit the severed tissue to be captured in said tissue receiving portion;

means for moving said cutting edge of said second tubular wall member between its first and second positions;

said second tubular wall member having an opening formed in its sidewall adjacent said cutting edge to provide internal communication between said annular passageway and said second bore to permit direct passage within said needle of irrigating fluid between said annular passageway and said second bore;

the forward portion of the sidewall of said first tubular wall member having no opening rearward of said cutting edge of said second tubular wall member when said cutting edge is in its first position;

means for providing the irrigating fluid to said annular passageway; and means for providing the source of suction to said second tubular wall member;

whereby the severed tissue is evacuated through said second bore with the aid of the irrigating fluid.

13. A percutaneous discectomy surgical instrument comprising:

a housing;

a needle supported by said housing, said needle having a forward portion extending distally of said housing;

said needle including a first elongated tubular wall member defining a first bore, and having a port formed entirely within the sidewall of the forward portion of said first tubular wall member;

said needle including a second elongated tubular wall member defining a second bore sized to permit passage of tissue therethrough when said second tubular wall member is connected to a source of suction, said second tubular wall member having a forward portion extending radially outwardly and terminating in a cutting edge;

said second tubular wall member being positioned within said first tubular wall member with said cutting edge in contact with the sidewall defining said first bore, the forward portion of said first bore adjacent said port defining a tissue receiving portion communicating with said second bore;

the wall of said second tubular wall member being spaced inwardly from the wall of said first tubular wall member to define the opposing walls of an annulus, said annulus providing the spacing for the forward portion of said second tubular wall member to extend radially outward and provide a cutting edge, said annulus being the sole annular space in said forward portion of said needle, a third elongated tubular wall member positioned in said second bore and defining a passageway adapted to be connected to a source of irrigating fluid, said passageway being in communication with said second bore;

said third elongated tubular wall member terminating approximately at said cutting edge of said second tubular wall member to provide direct passage within said needle of fluid between said third tubular wall member and said second bore;

said second tubular wall member being disposed for movement within said first tubular wall member to cause said cutting edge to move from a first position where tissue is drawn through said port into said tissue receiving portion of said first bore under suction to a second position where said cutting edge traverses said port to sever the tissue drawn therethrough, and to permit the severed tissue to be captured in said tissue receiving portion;

the forward portion of the sidewall of said first tubular wall member having no opening rearward of said cutting edge of said second tubular wall member when said cutting edge is in its first position;

whereby the severed tissue is evacuated through said second bore with the aid of the irrigating fluid.

* * * * *